United States Patent
Nair et al.

(10) Patent No.: US 9,607,730 B2
(45) Date of Patent: Mar. 28, 2017

(54) NON-OLEIC TRIGLYCERIDE BASED, LOW VISCOSITY, HIGH FLASH POINT DIELECTRIC FLUIDS

(71) Applicant: Dow Global Technologies LLC, Midland, MI (US)

(72) Inventors: Sreejit Nair, Mumbai (IN); Kaustubh S. Gupte, Mumbai (IN); Thomas S. Lin, Whippany, NJ (US); Jeffrey M. Cogen, Flemington, NJ (US); Bharat I. Chaudhary, Princeton, NJ (US); Anny L. Flory, Philadelphia, PA (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 14/432,929

(22) PCT Filed: Sep. 17, 2013

(86) PCT No.: PCT/US2013/060050
§ 371 (c)(1),
(2) Date: Apr. 1, 2015

(87) PCT Pub. No.: WO2014/062328
PCT Pub. Date: Apr. 24, 2014

(65) Prior Publication Data
US 2015/0243406 A1    Aug. 27, 2015

(30) Foreign Application Priority Data
Oct. 18, 2012  (WO) ............... PCT/IN2012/000692

(51) Int. Cl.
*H01B 3/20* (2006.01)
*A23D 9/00* (2006.01)
*C07C 69/533* (2006.01)

(52) U.S. Cl.
CPC ............... *H01B 3/20* (2013.01); *A23D 9/00* (2013.01); *C07C 69/533* (2013.01); *A23V 2250/00* (2013.01); *A23V 2250/188* (2013.01)

(58) Field of Classification Search
None
See application file for complete search history.

(56) References Cited

U.S. PATENT DOCUMENTS

| | | |
|---|---|---|
| 5,766,517 A | 6/1998 | Goedde et al. |
| 6,117,827 A | 9/2000 | Nagaoka et al. |
| 6,245,726 B1 | 6/2001 | Cannon et al. |
| 6,340,658 B1 | 1/2002 | Cannon et al. |
| 6,352,655 B1 | 3/2002 | McShane et al. |
| 6,398,986 B1 | 6/2002 | McShane et al. |
| 6,485,659 B1 | 11/2002 | Goedde et al. |
| 6,645,404 B2 | 11/2003 | Oommen et al. |
| 7,048,875 B2 | 5/2006 | Oommen et al. |
| 2006/0030499 A1 | 2/2006 | Oommen et al. |
| 2009/0140830 A1* | 6/2009 | Amanullah ............. H01B 3/22 336/94 |

FOREIGN PATENT DOCUMENTS

| | | |
|---|---|---|
| WO | 2004/108871 A2 | 12/2004 |
| WO | 2007/041785 A1 | 4/2007 |
| WO | 2011/090685 A1 | 7/2011 |
| WO | 2012/037366 A1 | 3/2012 |
| WO | 2012/110432 A1 | 8/2012 |

* cited by examiner

*Primary Examiner* — Necholus Ogden, Jr.
(74) *Attorney, Agent, or Firm* — Husch Blackwell LLP

(57) ABSTRACT

A vegetable-based dielectric fluid comprising in weight percent of triglycerides based on the weight of the fluid: A. Greater than 0 to 100% of at least one of C14:1 or C16:1 fatty acids; and at least one of: B. No more than (≤) 10% of C18:1 fatty acids; C. No more than (≤) 12% of one or more polyunsaturated fatty acids; and D. No more than (≤) 7% of one or more saturated fatty acids. The dielectric fluid is a useful transformer oil.

8 Claims, No Drawings

NON-OLEIC TRIGLYCERIDE BASED, LOW VISCOSITY, HIGH FLASH POINT DIELECTRIC FLUIDS

BACKGROUND OF THE INVENTION

1. Field of the Invention

This invention relates to dielectric fluids. In one aspect the invention relates to dielectric fluids comprising triglycerides of C14:1 and/or C16:1 fatty acids while in another aspect, the invention relates to dielectric fluids comprising triglycerides of C14:1 and/or C16:1 fatty acids in combination with one or more of polyunsaturated or saturated triglycerides and/or triglycerides of a C18:1 fatty acids.

2. Description of the Related Art

Vegetable oil (VO) based dielectric fluids, e.g., transformer fluids, have been increasingly used in the power generation industry to replace mineral oil (MO) based dielectric fluids because of their environmental friendliness and high flash point to improve safety of transformer operation. However, the VO-based dielectric fluids have significantly higher viscosity than the MO-based dielectric fluids, which results in a poorer heat transfer operation using a VO-based dielectric fluid. Therefore, a market need exists for a reduced viscosity VO-based dielectric fluid to improve the heat transfer efficiency in the transformer, while retaining the benefits of a high flash point combined with low melting point and low amounts of polyunsaturated fatty acids in the triglycerides.

Some of the conventional approaches to address this problem, and their associated disadvantages, include 1. Lowering the viscosity of VO-based dielectric fluid by blending it with lower viscosity fluids such as polyalphaolefins, synthetic polyol esters and polyglycerol fatty acid ester. However these approaches can lead to lowering of the flash point or to substituting with a non-natural based source;

2. Mixing the VO-based dielectric fluid with a diluent such as fatty acid alkyl ester, but this requires a diluent in excess of 10 weight percent (wt %) to reduce the viscosity of a canola oil to less than 33 centipoise (cP). However, this also results in lowering of the flash point;

3. Increasing the amount of unsaturation in the VO-based dielectric fluid lowers the viscosity of the fluid, but it also lowers the oxidation stability of the fluid (see U.S. Pat. No. 6,117,827); and 4. Increasing the amount of saturated C12-C16 triglycerides in the VO-based dielectric, but this also increases the melting point of the fluid.

Of continuing interest is a dielectric fluid that possesses a desired balance of properties, specifically a combination of low viscosity (≤33 cP at 40° C., ≤120 cP at 10° C.), high flash point (≥260° C., preferably ≥270° C.), and low melting point (−15° C. or less).

SUMMARY OF THE INVENTION

In one embodiment the invention is a composition of triglycerides comprising in weight percent based on the weight of the composition:

A. Greater than 0 to 100% of at least one of C14:1 or C16:1 fatty acids; and at least one of:
B. No more than (≤) 10% of C18:1 fatty acids;
C. No more than (≤) 12% of one or more polyunsaturated fatty acids; and
D. No more than (≤) 7% of one or more saturated fatty acids.

The triglyceride can comprise glycerol with any combination of the following fatty acids: C18:1, C14:1. C16:1, polyunsaturated and saturated. The fatty acids can attach to the glycerol molecule in any order, e.g., any fatty acid can react with any of the hydroxyl groups of the glycerol molecule to form an ester linkage. In one embodiment the compositions comprise at least two of the C18:1 fatty acid, polyunsaturated fatty acid and saturated fatty acid. In one embodiment the compositions comprise all three of the C18:1 fatty acid, polyunsaturated fatty acid and saturated fatty acid.

The compositions of this invention are useful as dielectric fluids, and exhibit a (i) viscosity of less than or equal to (≤) 33 cP at 40° C. and ≤120 cP at 10° C., (ii) flash point of greater than or equal to ≥260° C., preferably ≥270° C., and (iii) melting point of −15° C. or less.

In one embodiment the invention is an electrical device comprising a dielectric fluid in which the dielectric fluid is a composition of triglycerides comprising in weight percent based upon the weight of the composition:

A. Greater than 0 to 100% of at least one of C14:1 or C16:1 fatty acids; and at least one of:
B. No more than (≤) 10% of C18:1 fatty acids;
C. No more than (≤) 12% of one or more polyunsaturated fatty acids; and
D. No more than (≤) 7% of one or more saturated fatty acids.

The triglyceride can comprise glycerol with any combination of the following fatty acids: C18:1, C14:1, C16:1, polyunsaturated and saturated. The fatty acids can attach to the glycerol molecule in any order, e.g., any fatty acid can react with any of the hydroxyl groups of the glycerol molecule to form an ester linkage. In one embodiment the compositions comprise at least two of the C18:1 fatty acid, polyunsaturated fatty acid and saturated fatty acid. In one embodiment the compositions comprise all three of the C18:1 fatty acid, polyunsaturated fatty acid and saturated fatty acid.

DETAILED DESCRIPTION OF THE PREFERRED EMBODIMENT

Definitions

Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, temperature, is from 100 to 1,000, then all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, viscosity, temperature and the relative amounts of the individual components in the composition.

"Comprising", "including", "having" and like terms mean that the composition, process, etc. is not limited to the components, steps, etc. disclosed, but rather can include other, undisclosed components, steps, etc. In contrast, the term "consisting essentially of" excludes from the scope of any composition, process, etc. any other component, step etc. excepting those that are not essential to the performance, operability or the like of the composition, process, etc. The term "consisting of" excludes from a composition, process, etc., any component, step, etc. not specifically disclosed. The term "or", unless stated otherwise, refers to the disclosed members individually as well as in any combination.

"Dielectric fluid" and like terms mean a fluid, typically a liquid, that does not conduct, or conducts at a very low level, an electric current under normal circumstances. Vegetable oils inherently possess good dielectric properties (US 2006/0030499). For many vegetable oils the dielectric constant is less than 4.5.

"Viscosity" and like terms mean the resistance of a fluid which is being deformed by either sheer stress or tensile stress. For purposes of this specification, viscosity is measured at 40° C. and 10° C. using a Brookfield viscometer as measured by ASTM D-445.

"Flash point" and like terms mean the lowest temperature at which a volatile liquid can vaporize to form an ignitable mixture in air but will not continue to burn (compare to fire point). For purposes of this specification, flash point is measured by the method of ASTM D-3278.

"Fire point" and like terms mean the lowest temperature at which a volatile liquid can vaporize to form an ignitable mixture in air and will continue to burn after ignition. One accepted method for measuring the fire point of a liquid is ASTM D-92-12. The fire point of a liquid is typically 25-30° C. greater than the flash point.

"Pour point" and like terms mean the lowest temperature at which a liquid becomes semi-solid and loses its flow characteristics, or in other words, the minimum temperature at which a liquid will flow. For purposes of this specification, pour point is measured by ASTM D-97.

"Melting point" and like terms mean the temperature at which a material changes state from solid to liquid. For purposes of this specification, melting point is measured using a differential scanning calorimeter (DSC) and the following protocol:
 1. Equilibrate at 90.00° C.,
 2. Isothermal for 10 min,
 3. Ramp 2.00° C./min to −90.00° C.,
 4. End of cycle 1,
 5. Ramp 2.00° C./min to 90.00° C.,
 6. End of cycle 2,
 7. Ramp 2.00° C./min to −90.00° C.,
 8. End of cycle 3, and
 9. End of method.
The peak temperature of cycle 2 is reported as the melting point for the composition. Melting point correlates reasonably well with pour point.

"Triglyceride" and like terms mean an ester derived from glycerol and three fatty acids. The notation used in this specification to describe a triglyceride is the same as that used below to describe a fatty acid. The triglyceride can comprise glycerol with any combination of the following fatty acids: C18:1, C14:1, C16:1, polyunsaturated and saturated. The fatty acids can attach to the glycerol molecule in any order, e.g., any fatty acid can react with any of the hydroxyl groups of the glycerol molecule to form an ester linkage. Triglyceride of C18:1 fatty acid simply means that the fatty acid components of the triglyceride are derived from or based upon a C18:1 fatty acid. That is, a C18:1 triglyceride is an ester of glycerol and three fatty acids of 18 carbon atoms each with each fatty acid having one double bond. Similarly, a C14:1 triglyceride is an ester of glycerol and three fatty acids of 14 carbon atoms each with each fatty acid having one double bond. Likewise, a C16:1 triglyceride is an ester of glycerol and three fatty acids of 16 carbon atoms each with each fatty acid having one double bond. Triglycerides of C18:1 fatty acids in combination with C14:1 and/or C16:1 means that (a) a C18:1 triglyceride is mixed with a C14:1 triglyceride or a C16:1 triglyceride or both, or (b) at least one of the fatty acid components of the triglyceride is derived from or based upon a C18:1 fatty acid, while the other two are derived from or based upon C14:1 fatty acid and/or C16:1 fatty acid.

"Fatty acid" and like terms mean a carboxylic acid with a long aliphatic tail that is either saturated or unsaturated. Unsaturated fatty acids have one or more double bonds between carbon atoms. Saturated fatty acids do not contain any double bonds. The notation used in this specification for describing a fatty acid includes the capital letter "C" for carbon atom, followed by a number describing the number of carbon atoms in the fatty acid, followed by a colon and another number for the number of double bonds in the fatty acid. For example, C16:1 denotes a fatty acid of 16 carbon atoms with one double bond, e.g., palmitoleic acid. The number after the colon in this notation neither designates the placement of the double bond(s) in the fatty acid nor whether the hydrogen atoms bonded to the carbon atoms of the double bond are cis to one another. Other examples of this notation include C18:0 (stearic acid), C18:1 (oleic acid), C18:2 (linoleic acid), C18:3 (α-linolenic acid) and C20:4 (arachidonic acid).

Compositions

The first fatty acid component of the triglyceride compositions of this invention is at least one of a C14:1 or a C16:1. A C14:1 triglyceride is an ester of glycerol and three fatty acids of 14 carbon atoms each with each fatty acid having one double bond. Representative of the C14:1 fatty acids is myristoleic acid, physeteric acid and tsuzuic acid. A C14:1 triglyceride can comprise glycerol with any combination of three C14:1 fatty acids, and the C14:1 fatty acids can attach to the glycerol molecule in any order, e.g., any C14:1 fatty acid can react with any of the hydroxyl groups of the glycerol molecule to form an ester linkage. Typically, the C14:1 fatty acid is myristoleic acid.

A C16:1 triglyceride is an ester of glycerol and three fatty acids of 16 carbon atoms each with each fatty acid having one double bond. Representative of the C16:1 fatty acids is palmitoleic acid. Like the C14:1 triglyceride, a C16:1 triglyceride can comprise glycerol with any combination of three C16:1 fatty acids, and the C16:1 fatty acids can attach to the glycerol molecule in any order. Typically, the C16:1 fatty acid is palmitoleic acid.

The first fatty acid component of the triglyceride compositions of this invention can comprise 100% of either a C14:1 fatty acid or a C16:1 fatty acid or any combination of the two, e.g., 1-99 wt % of C14:1 fatty acid and 1-99 wt % of a C16:1 fatty acid, more typically the C14:1 fatty acid comprises 50 wt % of the combination.

The second fatty acid component of the triglyceride compositions of this invention is optional but if present, it is a C18:1, i.e., it contains 18 carbon atoms and has one double bond. Representative C18:1 fatty acids include oleic acid and vaccenic acid, with oleic acid preferred. A C18:1 triglyceride can comprise glycerol with any combination of three C18:1 fatty acids, e.g., three oleic acids, or two oleic acids and one vaccenic acid, or one oleic acid and two vaccenic acid. The three C18:1 fatty acids can attach to the glycerol molecule in any order. Typically, the three C18:1 fatty acids are oleic acid. In one embodiment the triglyceride compositions of this invention are free or void of any C18:1 fatty acids. In one embodiment the triglyceride compositions of this invention contain no more than 10 wt %, typically no more than 8 wt % and more typically no more than 5 wt %, of C18:1 fatty acids.

The third fatty acid component of the triglyceride compositions of this invention is optional but if present, it is polyunsaturated, i.e., a fatty acid of any carbon atom length, typically each of a length of at least 12 carbon atoms, and each fatty acid having more than one double bond. Like the C18:1 triglyceride, a polyunsaturated triglyceride can comprise glycerol with any combination of three polyunsaturated fatty acids, and the polyunsaturated fatty acids can attach to the glycerol molecule in any order. Representative polyunsaturated fatty acids from which the polyunsaturated triglyceride is made include, but are not limited to, linoleic acid (C18:2), α-linolenic acid (C18:3), γ-linolenic acid (C18:3), eicosadienoic acid (C20:2), dihomo-γ-linolenic acid (C20:3), arachidonic acid (C22:4), docosapentaenoic acid (C22:5), hexadecatrienoic acid (C16:3), heneicosapentaenoic acid (C21:5), rumenic acid (C18:2), α-calendic acid (C18:3), β-calendic acid (C18:3), α-parinaric acid (C18:4), β-parinaric acid, pinolenic acid (C18:3), podocarpic acid (C20:3), and the like. In one embodiment, the triglyceride compositions of this invention are free or void of any polyunsaturated fatty acids. In one embodiment, the third fatty acid component typically does not exceed 12 wt %, more typically it does not exceed 11 wt % and even more typically it does not exceed 10 wt %, of the composition.

The fourth fatty acid component of the triglyceride compositions of this invention is optional but if present, it is saturated triglyceride, i.e., an ester of glycerol and three fatty acids of any carbon atom length, typically each of a length of at least 8 carbon atoms, and each fatty acid free of any double bonds. Like the C18:1 triglyceride, saturated triglycerides can comprise glycerol with any combination of three saturated fatty acids, and the saturated fatty acids can attach to the glycerol molecule in any order. Representative saturated fatty acids from which the saturated triglyceride is made include, but are not limited to, lauric acid (C12:0), myristic acid (C14:0), palmitic acid (C16:0) and stearic acid (C18:0). In one embodiment the triglyceride compositions of this invention are free or void of any saturated fatty acids. In one embodiment the triglyceride compositions of this invention contain no more than 7 wt %, typically no more than 5 wt % and more typically no more than 3 wt %, of saturated fatty acids.

In one embodiment the compositions of this invention can comprise one or more additives such as one or more antioxidants, metal deactivators, pour point depressants, UV-stabilizers, water scavengers, pigments, dyes, and the like. Useful additives for dielectric fluids are well known in the art, and these additives, if used at all, are used in known ways and in known amounts. Typically the additives in the aggregate do not exceed 3 wt %, more typically do not exceed 2 wt % and even more typically do not exceed 1 wt % of the composition.

In one embodiment the invention is a composition of triglycerides consisting essentially of a in weight percent based on the weight of the composition:
   A. Greater than 0 to 100% of at least one of C14:1 or C16:1 fatty acids; and at least one of:
   B. No more than (≤) 10% of C18:1 fatty acids;
   C. No more than (≤) 12% of one or more polyunsaturated fatty acids; and
   D. No more than (≤) 7% of one or more saturated fatty acids.

In one embodiment the compositions contain at least two of the C18:1 fatty acids, polyunsaturated fatty acids and saturated fatty acids. In one embodiment the compositions contain all three of the C18:1 fatty acids, polyunsaturated fatty acids and saturated fatty acids. All of these "consisting essentially of" embodiments may contain one or more additives, e.g., antioxidant, metal deactivators, pour point depressant, pigment, etc., but it specifically excludes any triglycerides with fatty acids other than those identified or those present in inconsequential amounts, e.g., less than 10 wt % based on the weight of the composition. These "other" fatty acids, if present, are typically by-products or contaminants remaining after the desired fatty acid, e.g., a C14:1 or C16:1 fatty acid, is extracted from a natural source oil, e.g., corn oil, soy oil or the like. In other cases, the other fatty acids might be naturally present in the source oil.

In one embodiment the invention is an electrical device comprising a dielectric fluid in which the dielectric fluid is a composition of triglycerides consisting essentially of, in weight percent based upon the weight of the composition:
   A. Greater than 0 to 100% of at least one of C14:1 or C16:1 fatty acids; and at least one of:
   B. No more than (≤) 10% of C18:1 fatty acids;
   C. No more than (≤) 12% of one or more polyunsaturated fatty acids; and
   D. No more than (≤) 7% of one or more saturated fatty acids.

In one embodiment the dielectric fluid consists essentially of triglycerides of C14:1 fatty acids. In one embodiment the dielectric fluid consists essentially of triglycerides of C16:1 fatty acids. In one embodiment the dielectric fluid consists essentially of triglycerides of C14:1 and C16:1 fatty acids. In one embodiment the dielectric fluid consists essentially of triglycerides of C14:1 and/or C16:1 fatty acids in combination with at least one of not more than 10 wt % of C18:1 fatty acids, not more than 12 wt % of one or more polyunsaturated fatty acids, and not more than 7 wt % of one or more saturated fatty acids. In one embodiment the dielectric fluid consists essentially of triglycerides of C14:1 and/or C16:1 fatty acids in combination with at least two or all three of not more than 10 wt % of C18:1 fatty acids, not more than 12 wt % of one or more polyunsaturated fatty acids, and not more than 7 wt % of one or more saturated fatty acids. These "consisting essentially of" embodiments may contain one or more additives, e.g., antioxidant, pour point depressant, pigment, etc., but it specifically excludes any triglyceride with fatty acids other than those identified or those present in inconsequential amounts, e.g., less than 10 wt % based on the weight of the composition. These "other" fatty acids, if present, are typically by-products or contaminants remaining after the desired fatty acid, e.g., a C14:1 or C16:1 fatty acid, is extracted from a natural source oil, e.g., corn oil, soy oil or the like. In other cases, the "other" fatty acids might be naturally present in the source oil.

The triglycerides of the present invention may be obtained from vegetable and non-vegetable sources. The triglycerides used in the practice of this invention are typically derived from natural source oils, e.g., vegetable oil, algae oil, microbial oil, etc., with vegetable oils and algae oils being preferred natural source oils. These natural oils include, but are not limited to, those described in WO 2011/090685 and PCT/US2012/043973. These oils are typically rich in one or more particular triglycerides, the particular triglyceride dependent upon the particular vegetable oil or algae oil. For example, corn and soy oils are typically rich in triglycerides in which the fatty acid component is derived from oleic acid. The triglycerides used in the practice of this invention may be extracted from the vegetable or other natural source oil by any one of a number of known methods, e.g., solvent extraction, mechanical extraction, etc. In other cases, the source oil (e.g., algae oil) might in its entirety comprise the compositions of triglycerides of this invention, without a need for further isolation or extraction.

The compositions of this invention are particularly useful as dielectric fluids in various electrical equipment, e.g., as an insulating oil in transformers. The compositions of this invention are environmentally friendly, e.g., biodegradable, and possess a unique balance of properties, specifically a unique balance of viscosity, flash point and melting point.

The compositions of this invention are particularly useful as dielectric fluids in various electrical equipment, e.g., as an insulating oil in transformers. The compositions of this invention are environmentally friendly, e.g., biodegradable, and possess a unique balance of properties, specifically a unique balance of viscosity, flash point and melting point.

SPECIFIC EMBODIMENTS

The dynamic viscosity of pure triglyceride may also be obtained using a mathematical model based on the following factors:
1. Dynamic viscosity of methyl ester of fatty acid (FAME) which constitutes the triglyceride molecule.
2. Number of carbon atoms in the fatty acid chain of FAME.

$$\ln(\eta_{TAG}) = 0.5287 - 0.1542 * \eta_{FAME}1 - 0.1516 * \eta_{FAME}2 - $$
$$0.1542 * \eta_{FAME}3 - 1.5419 * \frac{1}{nCF_1} - 1.5158 * \frac{1}{nCF_2} - 1.5419 * \frac{1}{nCF_3} + $$
$$7.7064 * \frac{\eta_{FAME}1}{nCF_1} + 7.7188 * \frac{\eta_{FAME}2}{nCF_2} + 7.7064 * \frac{\eta_{FAME}3}{nCF_3}$$

Where
$\eta_{TAG}$=viscosity of triglyceride in cP
$\eta_{FAME}1$=viscosity of FAME present in the triglyceride at terminal position 1 in cP
$\eta_{FAME}2$=viscosity of FAME present in the triglyceride at central position 2 in cP
$\eta_{FAME}3$=viscosity of FAME present in the triglyceride at terminal position 3 in cP
$nCF_1$=number of carbon atoms in the fatty acid chain of FAME at terminal position 1
$nCF_2$=number of carbon atoms in the fatty acid chain of FAME at central position 2
$nCF_3$=number of carbon atoms in the fatty acid chain of FAME at terminal position 3

The viscosity of triglyceride mixture can be estimated as $$\ln\eta_{mix} = \sum_i w_i \cdot \ln\eta_i$$

$\eta_{mix}$=viscosity of triglyceride mixture in cP.
$w_i$=weight fraction of triglyceride 'i' in the triglyceride mixture.
$\eta_i$=viscosity of triglyceride i in the mixture in cP.

The melting point of pure triglyceride may also be obtained using a mathematical model based on the following factors:
1. Melting points of FAME which constitute the triglyceride molecule
2. Number of carbon atoms in fatty acid chain of FAME.
3. A descriptor to account for the similarity between terminal fatty acid chains (Terminal$_{Equal}$).

$$MP_{TAG} = -72.2053 + 0.3601 * MP_{FAME}1 + $$
$$0.4543 * MP_{FAME}2 + 0.3601 * MP_{FAME}3 + 578.4448 * \frac{1}{nCF_1} - $$
$$674.3624 * \frac{1}{nCF_2} + 578.4448 * \frac{1}{nCF_3} + 0.5813 * nCF_1 + $$
$$0.5813 * nCF_3 - 1.6560 * \frac{MP_{FAME}1}{nCF_1} - 1.6560 * \frac{MP_{FAME}3}{nCF_3} - $$
$$7.6588 * \frac{nCF_1}{nCF_2} - 7.6588 * \frac{nCF_3}{nCF_2} + 3.6244 * Terminal_{Equal} + $$
$$2.0464 * \frac{MP_{FAME}1}{nCF_2} + 2.0464 * \frac{MP_{FAME}3}{nCF_2}$$

Where
$MP_{FAME}1$=melting point of FAME present in the triglyceride at terminal position 1 in K
$MP_{FAME}2$=melting point of FAME present in the triglyceride at central position 2 in K
$MP_{FAME}3$=melting point of FAME present in the triglyceride at terminal position 3 in K
$nCF_1$=number of carbon atoms in fatty acid chain of FAME at terminal position 1
$nCF_2$=number of carbon atoms in fatty acid chain of FAME at central position 2
$nCF_3$=number of carbon atoms in fatty acid chain of FAME at terminal position 3.
Terminal$_{Equal}$=1 when the two terminal fatty acids fragments are the same or 0 when they are different.
The weight average melting point of triglyceride mixture can be estimated as $$MP_{mix} = \sum_i w_i \cdot MP_i$$

$MP_{mix}$=melting point of triglyceride mixture in K.
$w_i$=weight fraction of triglyceride 'i' in the triglyceride mixture.
$MP_i$=melting point of triglyceride 'i' in triglyceride mixture in K.
In all cases, the estimated (or predicted) weight average melting point is the same as that determined by DSC measurements or no more than 10° C. greater.
A further correction to the average melting point model was made by including degree of isomorphism ($\in$). The degree of isomorphism accounts for structural dissimilarity present in triglyceride mixtures which may result in lowering of melting points. The procedure of calculating ∈ is described in *Wesdorp, L. H. Liquid-multiple solid-phase equilibria in fats. Ph.D. Thesis, University Delft, The Netherlands,* 1990. For cis-unsaturated fatty acid fragments, the overlapping volume was decided by the projected length of cis-unsaturated fragment on straight chain saturated fragment. ∈ between different triglyceride pairs was calculated and the lowest of ∈, min(∈), was used as a model descriptor. min(∈) is an indicator of maximum dissimilarity present in triglyceride mixtures. The epsilon model for melting point prediction is given as $$MP_{epsilon\ model} = MP_{mix} 24.89 * \min(\in) - 24.89 (0 \leq \min(\in) \leq 1)$$

In all cases, the estimated (or predicted) epsilon melting point is the same as that determined by DSC measurements or no more than 10° C. greater.

The flash point of triglyceride or triglyceride mixtures may also be obtained using a mathematical model based on the heat of vaporization of pure triglyceride or triglyceride mixtures respectively.

$$\text{Flash Point}(K) = 45.004 \cdot [\Delta H^{vap}]^{0.50197}$$

Where
Flash point=Flash point of triglyceride in K
$\Delta H^{VAP}$=heat of vaporization of pure triglycerides or triglyceride mixtures in kJ/mol.
One of the representative methods to predict heat of vaporization of pure triglycerides is given in Chen et. al., Fragment-Based Approach for Estimating Thermophysical Properties of Fats and Vegetable Oils for Modeling Biodiesel Production Processes", Ind. Eng. Chem. Res. Vol. 49, Pg. 876-886, (2010).
The heat of vaporization of triglyceride mixtures can be determined using the following relationship $$\Delta H^{vap}_{mix} = \sum_{i} N_i \Delta H_i^{vap}$$

Where
$\Delta H^{vap}_{mix}$=heat of vaporization of the triglyceride mixture in kJ/mol
$N_i$=mole fraction of triglyceride i in the triglyceride mixture.
$\Delta H^{vap}_{,i}$=heat of vaporization of the triglyceride 'i' in kJ/mol Examples 1-10

The compositions reported in Table 1 are based on models built to predict the following properties of triglycerides and mixtures of triglycerides: viscosity, flash point and melting point. All examples exhibit the desired balance of viscosity ≤33 cP at 40° C. and ≤120 cP at 10° C., flash point ≥260° C., and melting point of −15° C. or less. The predicted melting point range provides the upper and the lower limit of the melting point of the mixture. This is based on the highest and lowest predicted melting points of the individual components of the composition. The melting points of the mixtures are determined by the methods mentioned above. Mixtures of triglycerides are highly interacting; hence the weight average is an approximate value of the melting point of the composition. The data on Example 5 show that the predicted melting points are identical to that determined experimentally by DSC. Similarly, there is very good agreement between the predicted and measured viscosities at 40° C. of Example 5.

TABLE 1

Examples 1 to 10

| Example # | C18:1 (wt %) | C18:2 (wt %) | C18:3 (wt %) | C16:1 (wt %) | C14:1 (wt %) | C18:0 (wt %) | Pred Visc (cP) (40 deg C.) | Pred Visc (cP) (10 deg C.) | Pred Flash Point (° C.) | MP (DSC) (° C.) | Pred MP Range (° C.) | Pred MP (wt avg) (° C.) | Pred MP (Epsilon model) (° C.) |
|---|---|---|---|---|---|---|---|---|---|---|---|---|---|
| 1 | | | | | | 100 | 17.1 | 54.75 | 275 | | −29 | −29 | −29 |
| 2 | | | | | 25 | 75 | 19.1 | 65.93 | 297 | | −29 < T < −24 | −24.5 | −28.3 |
| 3 | | | | | 50 | 50 | 21.15 | 77.1 | 289 | | −29 < T < −24 | −22.8 | −26.6 |
| 4 | | | | | 75 | 25 | 23.2 | 88.27 | 281.9 | | −29 < T < −24 | −24 | −27.8 |
| 5 | | | | | 100 | | 25.1/25 (expt) | 99.44 | 305 | −22.3 | T < −22 | −22.3 | −22.3 |
| 6 | 5 | | | | 95 | | 25.7 | 100.24 | 306.6 | | −24 < T < 0.5 | −21.2 | −24.5 |
| 7 | 10 | | | | 90 | | 26.2 | 101.04 | 306.2 | | −24 < T < 0.5 | −20 | −23.3 |
| | | | | | | Saturates | | | | | | | |
| 8 | | 8.5 | 1.5 | | | 85 | <5% | 20.2 | 69 | 280.5 | −29 < T < −13 | −22.5 | −22.5 |
| 9 | | 8.5 | 1.5 | 85 | | | <5% | 27.01 | 106.98 | 307 | −29 < T < −13 | −16.8 | −20.6 |
| 10 | 5 | 5 | | 85 | | | <5% | 27.8 | 109.8 | 306.8 | −24 < T < 0.5 | −16 | −23.7 |

Comparative Examples 1-18

In Table 2 Comparative Sample (CS) 1 to CS 10 are known triglyceride compositions. CS 2 and CS 3 reports compositions containing high amount of saturates, >7%, and do not provide the desired balance of properties, especially the melting point. CS 4 to CS 10 report properties of triglycerides of various fatty acids which do not yield the desired balance of properties with ≤2 wt % of polyunsaturated fatty acids. In particular, CS 7 and CS 8 provides balance of properties, but has polyunsaturated content >12% or are essentially triglycerides of polyunsaturated fatty acids.

Comparative Sample (CS) 11 to CS 18 are triglyceride compositions comprising varying amounts of diluents added to HOCO (High Oleic Canola oil). The composition of HOCO is:
1. Triglyceride containing C18 mono-unsaturated fatty acid=74%
2. Triglyceride containing C18 di-unsaturated fatty acid=14.5%

3. Triglyceride containing C18 tri-unsaturated fatty acid=4.5%
4. Triglyceride containing C18 saturated fatty acid=4%
5. Triglyceride containing C16 saturated fatty acid=3

SE 1185D is soy fatty acid methyl ester (FAME), NYCOBASE SEH is dioctyl sebacate, and PAO 2.5 is polyalphaolefin. The comparative samples with fatty acid compositions (CS 11 to CS 18) did not yield the desired combination of properties. In particular, CS 12 (HOCO: triglyceride with C18:1>70%, triglyceride with C18:2>14%, triglyceride with C18:3<3%) has a viscosity at 40° C.>33 cP (with flash point>300 deg C.). CS 13 to CS 18 reports compositions of HOCO with various diluents which do not yield the desired combination of properties.

TABLE 2

Comparative Examples 1-10

| Comparative Sample | C18:1 (wt %) | C18:2 (wt %) | C16:1 (wt %) | C14:1 (wt %) | C18:0 (wt %) | Pred Visc (cP) (40 deg C.) | Pred Visc (cP) (10 deg C.) | Pred Flash Point (° C.) | MP (DSC) (° C.) | Pred MP Range (° C.) | Pred MP (wt avg) (° C.) | Pred MP Epsilon model (° C.) |
|---|---|---|---|---|---|---|---|---|---|---|---|---|
| 1 | 15 | 85 | | | | 26.7 | 101.8 | 306.8 | | −24 < T < 0.5 | −18.9 | −22.2 |
| Saturates (Higher melting point) | | | | | | | | | | | | |
| 2 | 5 | 83 | | | 12 | 31 | 126.58 | 307 | | −24 < T < 72 | −9.8 | −16.4 |

From Oommen et al. (U.S. Pat. No. 7,048,875)

| CS # | C18:1 (wt %) | C18:2 (wt %) | C18:3 (wt %) | C18:0 (wt %) | C16:0 (wt %) | Pred Visc (cP) (40 deg C.) | Pred Visc (cP) (10 deg C.) | Pred Flash Pt (° C.) | MP (DSC) (oC) | Pred MP Range (° C.) | Pred MP (Wt. average) (° C.) | Pred MP Epsilon model (° C.) |
|---|---|---|---|---|---|---|---|---|---|---|---|---|
| 3 | 79 | 10 | 3 | 4 | 4 | 35.4 | 119.2 | 317.7 | −13 | −25 < T < 0.5 | 3.8 | −7.7 |

From McShane et al. (U.S. Pat. No. 6,352,655)

| CS # | C8:0 (wt %) | C10:0 (wt %) | C18:1 (wt %) | C18:2 (wt %) | C18:3 (wt %) | C18:0 (wt %) | C16:0 (wt %) | Pred Visc (cP) (40 deg C.) | Pred Visc (cP) (10 deg C.) | Pred Flash Pt (° C.) | MP (DSC) (° C.) | MP (Pred)-Weight Average (° C.) |
|---|---|---|---|---|---|---|---|---|---|---|---|---|
| 4 | 100 | | | | | | | | | 215 | | |
| 5 | | 100 | | | | | | | | 232 | | |
| 6 | | | 100 | | | | | 35.5 | 115.4 | 318.3 | | 0.5 |
| 7 | | | | 100 | | | | 23.1 | 71.4 | 318.3 | | −12.7 |
| 8 | | | | | 100 | | | 12.77 | 29.4 | 318.3 | | −24 |
| 9 | | | | | | 100 | | N/A | | N/A | | 72.5 |
| 10 | | | | | | | 100 | N/A | | N/A | | 63.6 |

| Concentration of Diluent in Mixture with HOCO | C18:1 triglyceride (wt %) | C18:2 triglyceride (wt %) | C14:1 and/or C16:1 triglyceride (wt %) | Experimental Dynamic Viscosity cP @ 40° C. | Experimental Dynamic Viscosity cP @10° C. | Experimental Flash Point (° C.) | Experimental Fire Point (° C.) | Experimental Pour Point (° C.) | Experimental Melting Point (° C.) | Predicted Dynamic Viscosity cP @ 40° C. | Predicted Flash Point (° C.) |
|---|---|---|---|---|---|---|---|---|---|---|---|
| CS 11 100 wt % Neobee 1053 | 0 | 0 | 0 | 13.8 | 50.1 | 250 | 284 | −9 | −4.4 | 14.7 | 222 (+/−3) |
| CS 12 0 wt % diluent | 74 | 14.5 | 0 | 33.2 | 132.2 | 324 | 350 | −15 | −13.3 | 34.4 | 318 (+/−)3 |
| CS 13 75 wt % Neobee 1053 | 18.5 | 3.6 | 0 | 17.5 | 66.0 | 260 | 290 | −15 | −17.5 | 19.6 | 239 (+/−3) |
| CS 14 100 wt % Nycobase SEH | 0 | 0 | 0 | 10.7 | 31.4 | 224 | 257 | −66 | | | |
| CS 15 15 wt % SEH | 62.9 | 12.3 | 0 | 29.4 | 104.5 | 282 | 302 | N/A | | | |
| CS 16 25 wt % SEH | 55.5 | 10.9 | 0 | 26.4 | 90.9 | 266 | 288 | N/A | | | |
| CS 17 15 wt % SE 1185D (soy FAME) | 62.9 | 12.3 | 0 | 24.1 | 78.1 | 236 | 256 | N/A | | | |

TABLE 2-continued

Comparative Examples 1-10

| | | | | | | | | |
|---|---|---|---|---|---|---|---|---|
| CS 18 15 wt % PAO 2.5 | 62.9 | 12.3 | 0 | 26.8 | 92.7 | 234 | 250 | N/A |

TABLE 3

Comparison of Properties of Various Vegetable Oils

| | Viscosity (cp) at 40 deg C. | Flash Point (deg C.) | Melting point (deg C.) | Polyunsaturated content (%) |
|---|---|---|---|---|
| Castor | >33 | >300 | | |
| Coconut | | | 25 | |
| Corn | | >300 | | >50% |
| Cottonseed | | | | >50% |
| Crambie | >33 | | | |
| Jojoba | Non triglyceride containing components | | | |
| Lesquerella | >33 | | | |
| Linseed | | | | >50% |
| Olive | >33 | | >−15 | |
| Palm | | | >−15 | |
| Rapeseed (Canola) | | >300 | | >30% |
| Safflower | | >300 | | >50% |
| Sunflower | | >300 | | >50% |
| Soya | | >300 | | >30% |
| Veronia | Functionalized triglycerides (epoxidized fatty acids) | | | |

Table 3 reports the properties of various natural oils, none of which exhibit the desired balance. In particular corn oil, cottonseed oil, linseed oil, canola oil, safflower oil, sunflower oil, and soy oil have high content of triglycerides of polyunsaturated fats (>15%) while castor, crambie, lesquerella, and olive have high viscosity (>33 cP), and coconut oil and palm oil have high melting points.

Although the invention has been described with certain detail through the preceding description of the preferred embodiments, this detail is for the primary purpose of illustration. Many variations and modifications can be made by one skilled in the art without departing from the spirit and scope of the invention as described in the following claims.

What is claimed is:

1. A dielectric fluid composition of triglycerides comprising in weight percent based on the weight of the composition:
   A. Greater than 0 to 100% of at least one of C14:1 or C16:1 fatty acids; and at least one of:
   B. No more than (≤) 10% of C18:1 fatty acids;
   C. No more than (≤) 12% of one or more polyunsaturated fatty acids; and
   D. No more than (≤) 7% of one or more saturated fatty acids and wherein the composition has a viscosity of equal to or less than (<) 33 cP at 40° C. and equal to or less than (<) 120 cP at 10° C.; a flash point of equal to or greater than (>) 260° C.; and a melting point of equal to or less than (<) −15° C.

2. The composition of claim 1 comprising at least two of the fatty acids of (B), (C) and (D).

3. The composition of claim 1 comprising all three of the fatty acids of (B), (C) and (D).

4. A dielectric fluid composition of triglycerides consisting essentially of, in weight percent based on the weight of the composition:
   A. Greater than 0 to 100% of at least one of C14:1 or C16:1 fatty acids; and at least one of:
   B. No more than (≤) 10% of C18:1 fatty acids;
   C. No more than (≤) 12% of one or more polyunsaturated fatty acids; and
   D. No more than (≤) 7% of one or more saturated fatty acids and wherein the composition has a viscosity of equal to or less than (<) 33 cP at 40° C. and equal to or less than (<) 120 cP at 10° C.; a flash point of equal to or greater than (>) 260° C.; and a melting point of equal to or less than (<) −15° C.

5. An electrical device comprising a dielectric fluid in which the dielectric fluid is a composition of triglycerides comprising in weight percent based upon the weight of the composition:
   A. Greater than 0 to 100% of at least one of C14:1 or C16:1 fatty acids;
   B. No more than (≤) 10% of C18:1 fatty acids;
   C. No more than (≤) 12% of one or more polyunsaturated fatty acids; and
   D. No more than (≤) 7% of one or more saturated fatty acids and wherein the composition has a viscosity of equal to or less than (<) 33 cP at 40° C. and equal to or less than (<) 120 cP at 10° C.; a flash point of equal to or greater than (>) 260° C.; and a melting point of equal to or less than (<) −15° C.

6. The electrical device of claim 5 in which the dielectric fluid consists essentially of a triglyceride of C14:1 and/or C16:1 fatty acid.

7. The electrical device of claim 5 in which the dielectric fluid consists essentially of triglycerides of:
   A. Greater than 0 to 100% of at least one of C14:1 or C16:1 fatty acids;
   B. No more than (≤) 10% of C18:1 fatty acids;
   C. No more than (≤) 12% of one or more polyunsaturated fatty acids; and
   D. No more than (≤) 7% of one or more saturated fatty acids.

8. The electrical device of claim 5 in which the dielectric fluid comprises 100 wt % of the at least one of C14:1 or C16:1 fatty acids.

* * * * *